(12) United States Patent
Drevik

(10) Patent No.: US 6,554,812 B2
(45) Date of Patent: *Apr. 29, 2003

(54) SANITARY NAPKIN

(75) Inventor: Solgun Drevik, Molnlycke (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/833,629

(22) Filed: Apr. 13, 2001

(65) Prior Publication Data

US 2001/0031956 A1 Oct. 18, 2001

Related U.S. Application Data

(60) Provisional application No. 60/200,356, filed on Apr. 28, 2000.

(30) Foreign Application Priority Data

Apr. 13, 2000 (SE) ............................................... 0001376

(51) Int. Cl.[7] ............................................................. A61F 13/15
(52) U.S. Cl. ................................... 604/385.04; 604/387
(58) Field of Search .......... 604/385.01, 385.03–385.05, 604/386, 387

(56) References Cited

U.S. PATENT DOCUMENTS 5,037,417 A * 8/1991 Ternstrom et al. ..... 604/385.25
5,713,886 A * 2/1998 Sturino ................... 604/385.04
5,729,835 A * 3/1998 Williams ........................ 2/400
6,443,934 B1 * 9/2002 Glaug et al. ........... 604/385.04

FOREIGN PATENT DOCUMENTS

| DE | 198 34785 | | 2/2000 | |
| WO | WO 00/30585 | * | 2/2000 | ........... A61F/13/45 |

* cited by examiner

*Primary Examiner*—Dennis Ruhl
*Assistant Examiner*—Jamisue A. Webb
(74) *Attorney, Agent, or Firm*—Young & Thompson

(57) ABSTRACT

An absorbent article includes outwardly projecting, flexible flaps which extend beyond respective sides of an absorbent body along a tapering part of the body and have outer longitudinal edges which in the unfolded state of the flaps are inclined relative to the longitudinal symmetry axis (A—A) of the article at an angle α such that the distance between the outer sides of the flaps and the longitudinal symmetry axis of the article decreases in a direction towards the rear end of the article. The angle (α) is larger than the angle (β) at which a first imaginary line inclined to the longitudinal symmetry axis, and passing through the outer limitation point of the absorbent body in its widest part and the outer transversal limitation point of the rear end of the absorbent body.

9 Claims, 1 Drawing Sheet

SANITARY NAPKIN

FIELD OF INVENTION

The present invention relates to an absorbent article such as a sanitary napkin, a panty liner or an incontinence protector for women, comprising an absorbent body that is sandwiched between a liquid-permeable and a liquid-impermeable outer sheet, wherein the article has a front part, which is intended to face forwards when the article is worn, and a rear part, wherein the absorbent body tapers rearwardly from a section of widest width situated in the front part of the article to the end of the rear part thereof, and wherein the ratio between the broadest part of the absorbent body and its narrowest part is greater than 2.

BACKGROUND OF THE INVENTION

A sanitary napkin of this kind is intended to be worn inside so-called string panties, which are extremely narrow in the rear part of the crotch portion of the napkin. It is also desirable to provide sanitary napkins intended for string panties with outwardly projecting wings or flaps that can be folded around the edges of a pair of panties and fastened to the outside thereof and/or to each other, as such flaps have been widely accepted in the case of napkins that are intended to be worn under conventional panties or underpants. It is also important that the narrow rear part of the absorbent body is held securely in a correct position when worn so as to avoid leakage, and it is therefore necessary to design and position the fastener flaps in a manner which facilitates correct positioning of the narrow rear part of the absorbent body when placing the napkin in a pair of string panties.

The present invention aims to design the flaps of a flap-equipped absorbent article in the form of a sanitary napkin, a panty liner or an incontinence protector for women intended to be worn in a pair of string panties so as to facilitate correct positioning and safe retention of the rear part of the article when the article is worn. Another aim of the invention is to provide flaps that when the napkin is worn are able to follow the edges of the panties in the crotch part thereof, therewith enabling the napkin to be placed readily in position and providing maximum security in wear.

SUMMARY OF THE INVENTION

These aims are achieved with an absorbent article in the form of a sanitary napkin, a panty liner or an incontinence protector for women that includes an absorbent body or pad sandwiched between a liquid-permeable and a liquid-impermeable outer sheet and which includes a front part that is intended to face forwards when the article is worn, and a rear part, wherein the absorbent body tapers rearwardly to the end of said rear part, from a section of widest width situated in the front part of the article, and wherein the ratio between the widest part of the absorbent body and its narrowest part is greater than 2, wherein said absorbent article is characterised in that the article includes outwardly projecting flaps made of flexible material and extending outwardly on respective sides of the absorbent body along a portion of the narrowing part of said body, wherein said flaps have outer longitudinally extending edges which in the unfolded state of the flaps are inclined relative to the longitudinal symmetry axis of said article at an angle such that the distance between the outer sides of said flaps and the longitudinal symmetry axis of the article will decrease in a direction towards the rear end of the article, wherein the outer longitudinally extending edges of the flaps in the unfolded state of said flaps are each inclined to the longitudinal symmetry axis of the article at a first angle which is greater than the angle of slope to the longitudinal symmetry axis of a first imaginary line that passes through the outer limitation point of the absorbent body in its widest part and the outer limitation point transversely of the rear end of the absorbent body on the same side of the longitudinal symmetry axis as the edge in question, but which is smaller than three times said slope angle. Flaps of this design enable the available surface area of the string panty to be utilised to a maximum for fastening the rear part of the absorbent article while ensuring that an inwardly folded flap will not extend beyond the side edges of the article.

In one preferred embodiment, the first angle is equal to or greater than two times the angle at which the first imaginary line is inclined to the longitudinal symmetry axis, and the width of the fastener flaps at their widest part is equal to or smaller than half the width of the absorbent body in that part thereof which, in the longitudinal direction, lies level with the points at which side edges of the absorbent body intersect two second imaginary lines that extend perpendicularly to the first imaginary lines from respective widest points of the fastener flaps. At least two strings of adhesive are applied to at least one of the flaps on that side thereof which lies on the same side of the article as the liquid-impermeable outer sheet when the flap is unfolded, said strings extending parallel with the longitudinal symmetry axis of the article and being mutually offset both longitudinally and transversely, wherein when the article is flat each rearwardly lying string of adhesive will be situated closer to the longitudinal symmetry line of the article than the forwardly lying string. The flaps preferably form integral parts of the outer sheets. At least one string of adhesive is applied to that part of the sanitary napkin that includes the absorbent body. The adhesive strings consist suitably of a pressure-sensitive glue, conveniently a hotmelt glue. The strings of adhesive applied on the flaps will conveniently overlap each other in the longitudinal direction and are preferably rectangular in shape. An imaginary line that extends through the outermost corners of the strings on the same flap as seen transversely will preferably have the same angle of inclination to the longitudinal symmetry axis of the article as the outer longitudinally extending edge of said flap, whereas an imaginary line through the innermost corners of the adhesive strings on said one and the same flap as seen transversely will have a smaller angle of inclination to the longitudinal symmetry axis of the article than the outer longitudinal edge of said flap.

BRIEF DESCRIPTION OF THE DRAWINGS

The invention will now be described in more detail with reference to the accompanying drawings, in which.

DESCRIPTION OF EMBODIMENTS

Figure 1:
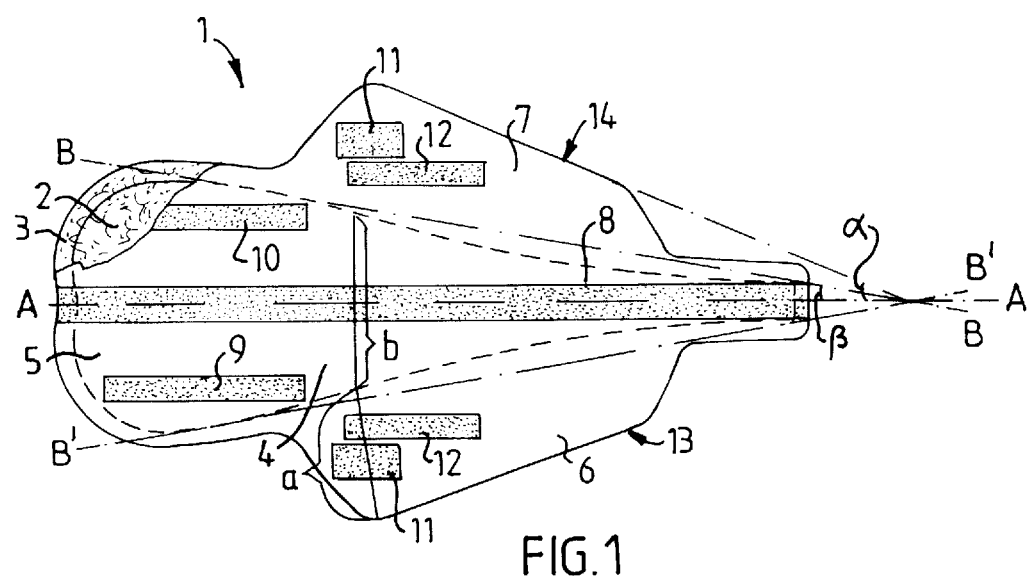
FIG. 1 is a schematic, partially sectioned plan view of a sanitary napkin according to a first embodiment of the invention, with the fastener flaps shown unfolded.

The sanitary napkin 1 illustrated in FIG. 1 typically includes an absorbent body or pad 2 which is sandwiched between a liquid-permeable outer sheet 3 and a liquid-impermeable outer sheet or backing sheet 4. The outer sheets 3, 4 are mutually joined at parts which lie outside the absorbent body, suitably by gluing or ultrasound welding or heat welding.

The sanitary napkin 1 is designed so that it can be worn in a pair of string panties, and the absorbent body 2 therefore tapers rearwardly from the widest part of the front portion 5 of the napkin to the rear end thereof. The ratio between the widest part of the absorbent body and its narrowest part is greater than 2, preferably greater than 3. The outer sheets 3, 4 form outwardly projecting flaps 6, 7 or wings, which are arranged so that they can be folded around the edges of the panties and fastened to the outside thereof.

The flaps 6, 7 extend longitudinally outwardly of the edges of the absorbent body, and the longitudinal edges of the flaps therewith converge mutually in the rearward direction. In the illustrated case, the flaps have a length which corresponds to about half the length of the napkin and are spaced wider apart from the forward end of the napkin than from its rear end. FIG. 1 shows the shows the flaps 6, 7 unfolded. In the unfolded state of the flaps their longitudinal edges 13, 14 are inclined at an angle $\alpha$ to the longitudinal symmetry axis A—A of the napkin, and imaginary lines B—B, B'—B' that pass through the outermost limitation points of the absorbent body in the front portion 5 of the article and in the rear end-portion of the absorbent body respectively are inclined at an angle $\beta$ to said longitudinal symmetry axis A—A. It will be seen from FIG. 1 that the angle $\alpha$ is larger than the angle $\beta$.

The illustrated sanitary napkin has a length of 140–260 mm and the absorbent body has a widest width of 70 mm and a smallest width of about 10 mm at its rear end. The flaps extend between about 25–30 mm outwardly of the edges of the absorbent body, with the greatest distance being at the front parts of the flaps. The front edges of the flaps are located about 60 mm from the front edge of the napkin, while their rear edges are located about 50 mm from the rear end of said napkin. It will be understood that the aforesaid measurements are merely given to provide a qualitative understanding of an appropriate configuration or design of a sanitary napkin intended for string panties and in no way limit the scope of the invention.

The liquid-permeable outer sheet 3 is comprised of a soft, skin-friendly material. This outer sheet may comprise a sheet of different types of nonwoven material. Alternative materials in this respect are perforated plastic films, plastic nets, knitted, crocheted or woven materials, and combinations and laminates of these types of materials. The plastic may be a thermoplastic, e.g. polyethylene (PE). The nonwoven material may comprise natural fibres, such as cellulose or cotton, although it may alternatively comprise synthetic fibres, such as polyethylene (PE), polypropylene (PP), polyurethane (PU), a polyester, nylon or regenerated cellulose, or a mixture of different fibres. All materials that are used to provide liquid-permeable outer sheets in absorbent articles, such as sanitary napkins, panty liners or incontinence protectors, can be used for the liquid-permeable outer sheet 3, and it will be understood that the aforesaid materials are given merely by way of example.

The liquid-impermeable backing sheet 4 consists of a flexible material, preferably a thin film of polyethylene (PE), polypropylene (PP) or polyester, although it may also comprise a lamination of nonwoven material with liquid-impermeable material. All materials that are typically used to produce liquid-impervious backing sheets for absorbent articles can be used. The backing sheet 4 may conveniently be air-permeable.

The absorbent body 2 is preferably constructed from cellulose fibres, although other natural materials may be used, such as cotton fibres or peat. Alternatively, absorbent synthetic fibres or a mixture of natural fibres and synthetic fibres may be used. The absorbent body 2 may also include a superabsorbent, i.e. a polymer that is able to absorb liquid in an amount corresponding to several times its own weight. The absorbent body may also include shape-stabilising means and liquid-dispersing means, and also a binder which functions to hold short fibres and particles together such as to provide a coherent unit. The absorbent body may also be comprised of more than one layer of absorbent material.

In the illustrated embodiment, the flaps 6, 7 are comprised of laterally extended portions of the outer sheets 3, 4, although they may be comprised of extended portions of solely one of said sheets, preferably the liquid-impermeable backing sheet in such case. The flaps may also consist of separate pieces of material that are fastened to the sides of the napkin 1.

The sanitary napkin 1 is provided with three adhesive strings 8, 9, 10 on the liquid-impermeable backing sheet 4, in the area of the absorbent body 2. These adhesive strings include a central adhesive string 8 that extends along the longitudinal symmetry axis A—A of the napkin over its full length, and two shorter adhesive strings 9, 10 that extend on respective opposite sides of the central adhesive string 8, in the front part 5 of the napkin. These adhesive strings 8, 9, 10 are intended for fastening the sanitary napkin 1 to the inside of a pair of string panties. Each of the adhesive strings 8, 9, 10 extends parallel with the longitudinal symmetry axis A—A of the sanitary napkin 1.

The sanitary napkin 1 is also provided with two adhesive strings 11, 12 on each flap 6, 7. These adhesive strings 11, 12 are relatively short and extend in directions parallel with the longitudinal symmetry axis A—A of the napkin when the napkin is flat. The adhesive strings 11, 12 on each flap 6, 7 are also mutually spaced both longitudinally and laterally, wherewith the foremost string 11 is situated farthest from the longitudinal symmetry axis A—A. Although the FIG. 1 embodiment includes only two adhesive strings 11, 12 on each flap 6, 7, it will be understood that the flaps may be provided with more than two strings if so desired. The adhesive strings 11, 12 on the flaps 6, 7 are rectangular in shape and an imaginary line passing through the transversely outermost corners of the strings on one and the same flap is inclined to the longitudinal symmetry axis A—A of the article at the same angle as the outer longitudinal edge of said flap, whereas an imaginary line passing through the transversely innermost corners of the strings on one and the same flap has a smaller angle of inclination to the longitudinal symmetry axis A—A than the outer longitudinal edge of said flap.

The adhesive used in the adhesive strings is a pressure-sensitive hotmelt glue, e.g. Ecomelt H145 from Collano, Switzerland. However, it is possible to use other commercially available pressure-sensitive adhesives, and also adhesives that are pressure-sensitive in a cold state, such as acrylate glue, normally combined with additives that enhance the stickiness of the glue, such as polyterpene or hotmelt glue, such as styrene and butadiene co-polymers.

The imaginary lines B—B and B'—B' form the natural folding lines of the flaps 6, 7 and no adhesive should therefore be applied inwardly of these lines. An adhesive-free area should also be provided adjacent the edges 13, 14 of the flaps, so as to facilitate handling of the flaps by the user. The flaps will also have a width that ensures that the flaps will not extend beyond the edges of the absorbent body when folded. This means that only a limited area is available on the flaps for the application of adhesive. Because the angle α is larger than the angle β, the surface area that is available for the application of adhesive is larger in the forward part of the flaps than the case when the edges 13, 14 are allowed to extend parallel with the lines B—B, B'—B'.

The sanitary napkin of the described embodiment includes flaps 6, 7 that are intended to be fastened to the outside of a string panty subsequent to being folded-in. In the illustrated case, the angle α is two times the size of the angle β. Furthermore, the width a of the fastener flaps 6, 7 at their widest part is equal to half the width of the absorbent body 2 in that part of said body that is longitudinally level with the points at which the side edges of the absorbent body are intersected by two second imaginary lines that extend perpendicularly to the first imaginary lines B—B, B'—B' from respective widest points of the fastener flaps 6, 7.

Figure 2:
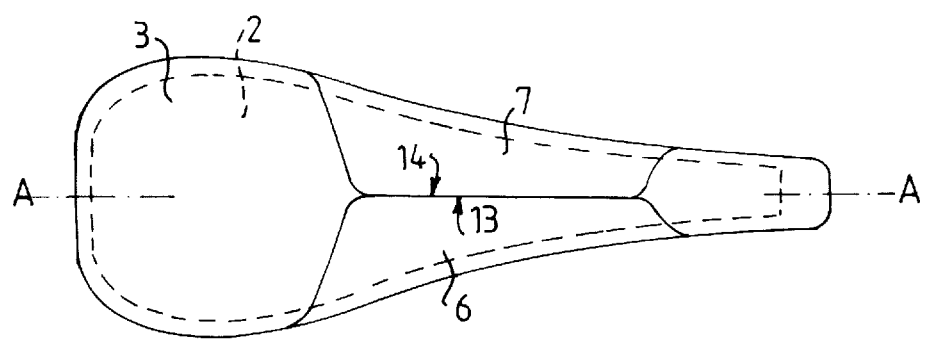
FIG. 2 illustrates the sanitary napkin of FIG. 1 schematically and in plan view, with the fastener flaps folded-in in a packaging state.

FIG. 2 shows the sanitary napkin 1 with the flaps 6, 7 folded in over the liquid-permeable outer sheet 3, which is normal when the napkin is folded for packaging purposes. As will be evident from this schematic Figure, the inwardly folded flaps extend along the longitudinal symmetry axis A—A. This enables practically all of the surface area of the flaps to be utilised in fastening the napkin to a string panty. Furthermore, such a configuration gives the user an indication of whether or not the flaps are correctly folded, wherewith the user finds it easier to position the napkin correctly in her panty. When the width a is greater than half the width b the flaps 6, 7 will overlap each other, which is undesirable aesthetically and also constitutes a waste of material. Overlapping flaps can also present problems to the user, particularly in deciding how large the overlap should be. When the width a is equal to half the width b and the longitudinal edges 13, 14 of the flaps slope at an angle α that is larger than two times the angle β, the longitudinal edges 13, 14 will diverge mutually in the rearward direction of the napkin, which is not preferred because it results in a reduction in the surface area available for application of an adhesive. When the width a is equal to half the width β and the longitudinal edges 13, 14 of the flaps slope at an angle α that is smaller than two times the angle β, the longitudinal edges 13, 14 will overlap mutually to an increasing extent in the rearward direction, which may be desirable provided that the overlap does not cause part of the adhesive strings disposed on the rear portions of the flaps to fasten to an inwardly folded flap instead of to the outside of the string panty.

In the package state of the sanitary napkin, the adhesive strings are covered with a protective layer, e.g. with release paper comprising a silicone-coated paper and functioning to protect the adhesive strings against contaminants, such as dust and similar substances, and also to prevent the adhesive from drying out prior to use. The napkin 1 is conveniently provided with a central protective layer which is not removed until the napkin shall be fastened to the inside of a string panty, and a protective layer on each flap, these latter layers being removed prior to folding the flap around the edge of a string panty and fastening said flaps to the outside thereof. These protective layers have not been shown in the Figures for the sake of clarity.

It is also conceivable to design the fastener flaps so that when folded inwards they fasten to each other instead of to the outside of a string panty. In this case, the width a should not exceed the width b and the angle α should not be greater than three times the angle β.

The described embodiments may, of course, be modified within the scope of the invention. For instance, the absorbent body may include a central upwardly projecting part and the napkin may have dimensions other than those mentioned above. Furthermore, the glue pattern on that part of the napkin which includes the absorbent body may be configured differently, for instance the central adhesive string need not extend over the whole of the front part of the napkin and the three adhesive strings disposed on the front part of the napkin may be replaced with one single glue string that extends over the major part of the front portion of the diaper. That part of the napkin which includes the absorbent body may be provided with more than three adhesive strings. It is also conceivable to replace the adhesive strings in the region of the absorbent body with friction coatings or similar coatings. It is also possible to use touch-and-close material of the type that fasten to textile-like material instead of adhesive strings. It will therefore be understood that the invention is solely limited by the contents of the accompanying claims.

What is claimed is:

1. An absorbent article selected from the group consisting of a sanitary napkin, a panty liner and an incontinence protector for women, comprising an absorbent body that is sandwiched between a liquid-permeable outer sheet and a liquid-impermeable outer sheet; said article having a front part intended to face forwards when the article is worn, and a rear part; said absorbent body having a front end edge, a rear end edge, and two side edges continuously tapering rearwardly from a widest part situated in the front part off the article between said side edges to a narrowest part situated at an end of the rear part of the article between said side edges; the ratio between the distance between the side edges in the widest part of the absorbent body and the distance between the side edges in its narrowest part being greater than 2; said article including outwardly projecting flexible flaps which extend outwardly of the absorbent body and have outer longitudinal edges, which in an unfolded state of the flaps are inclined relative to a longitudinal symmetry axis of the article at a first angle such that the distance between the outer longitudinal edges of said flaps and the longitudinal symmetry axis will decrease in a direction towards the rear end of the article; said first angle being larger than a second angle at which a first imaginary line is inclined to the longitudinal symmetry axis, said first imaginary line passing through an outer limitation point of the absorbent body at its widest part and an outer limitation point transversely of the rear end of the absorbent body at its narrowest part on the same side of the longitudinal symmetry axis as a corresponding longitudinal outer edge; and said first angle being smaller than three times the second angle.

2. The absorbent article according to claim 1, wherein the first angle is equal to or smaller than two times the second angle at which the first imaginary line is inclined to the longitudinal symmetry axis.

3. The absorbent article according to claim 1, wherein the flaps have a widest part whose width is equal to or smaller than, half the width of the absorbent body in that part of said absorbent body that is longitudinally level with points at which two second imaginary lines intersect side edges of the absorbent body; said second imaginary lines extending perpendicularly to the first imaginary lines from respective widest points of the flaps.

4. The absorbent article according to claim 1, wherein the flaps are integral parts of at least one of the liquid-impermeable outer sheet and the liquid-permeable outer sheet.

5. The absorbent article according to claim 1, further comprising at least one adhesive string on that part of the article which includes the absorbent body.

6. The absorbent article according to claim 1, wherein at least one of the flaps comprises at least two strings of adhesive including a rearwardly lying string of adhesive and a forwardly lying string of adhesive, on that side of said at least one of the flaps which lies on the same side of the article as the liquid-impermeable outer sheet in the unfolded state of the flaps; said strings of adhesive extending parallel to the longitudinal symmetry axis of the article and being offset longitudinally and laterally in relation to each other, and wherein when the article is flat said rearwardly lying string of adhesive will be situated closer to the longitudinal symmetry axis than the forwardly lying string of adhesive.

7. The absorbent article according to claim 6, wherein the strings of adhesive overlap each other longitudinally.

8. The absorbent article according to claim 6, wherein the strings of adhesive are comprised of pressure-sensitive glue.

9. The absorbent article according to claim 6, wherein the strings of adhesive are comprised of a hotmelt glue.

* * * * *